United States Patent
Hill et al.

(10) Patent No.: US 9,512,163 B2
(45) Date of Patent: Dec. 6, 2016

(54) COMPOSITIONS AND METHODS FOR CONJUGATING OLIGONUCLEOTIDES

(71) Applicant: Agilent Technologies, Inc., Loveland, CO (US)

(72) Inventors: Kenneth W. Hill, Lyons, CO (US); Victor R Mokler, Golden, CO (US)

(73) Assignee: Agilent Technologies, Inc., Santa Clara, CA (US)

( * ) Notice: Subject to any disclaimer, the term of this patent is extended or adjusted under 35 U.S.C. 154(b) by 0 days.

(21) Appl. No.: 14/402,220

(22) PCT Filed: Apr. 29, 2013

(86) PCT No.: PCT/US2013/038703
§ 371 (c)(1),
(2) Date: Nov. 19, 2014

(87) PCT Pub. No.: WO2013/176844
PCT Pub. Date: Nov. 28, 2013

(65) Prior Publication Data
US 2015/0133631 A1     May 14, 2015

Related U.S. Application Data

(60) Provisional application No. 61/649,766, filed on May 21, 2012.

(51) Int. Cl.
| | |
|---|---|
| C07H 21/00 | (2006.01) |
| C07K 19/00 | (2006.01) |
| C07H 1/00 | (2006.01) |
| C07H 21/02 | (2006.01) |

(52) U.S. Cl.
CPC .............. *C07H 21/00* (2013.01); *C07H 1/00* (2013.01); *C07H 21/02* (2013.01); *C07K 19/00* (2013.01)

(58) Field of Classification Search
CPC ................................ C07H 21/00; C07K 19/00
See application file for complete search history.

(56) References Cited

U.S. PATENT DOCUMENTS

| 6,140,494 A | 10/2000 | Hamilton et al. |
| 2011/0092806 A1 | 4/2011 | Port et al. |

FOREIGN PATENT DOCUMENTS

| CN | 102459301 A | 5/2012 |
| JP | 2005247706 | 9/2005 |
| WO | WO9830575 | 7/1998 |
| WO | WO2009156421 | 12/2009 |
| WO | WO2013176845 | 11/2013 |

OTHER PUBLICATIONS

Sato et al., Eur. J. Org. Chem., 2004, p. 2142-2150.*
Veronese et al., Drug Discovery Today, 2005, 10(21), p. 1451-1458.*
Didenko et al., Am. J. Pathol., 1998, 152(4), p. 897-902.*
Drosdziok et al., J. Label Compd. Radiopharm., 2003, 46, p. 815-835.*
Sato, et al, "Synthesis and properties of a new oligonucleotide analogue containing an internucleotide squaryl amide linkage", Nucleic Acids Research Supplement No. 1 121-122.
Wurm, et al, "Squaric acid mediated synthesis and biological activity of a library of linear and hyperbranched poly (glycerol)-protein conjugates", Biomacromolecules. Apr. 9, 2012;13(4):1161-71.
Zhao, et al, "Preparation of mannosylated oligoribonucleotides", Nucleic Acids Symp Ser (Oxf). 2008;(52):89-90.
Zhao, et al, "Synthesis and characterization of mannosylated oligoribonucleotides", Carbohydr Res. 2009, 344(16):2137-43.
Yan, et al. "Bioorganic & Medicinal Chemistry Letters",vol. 17, Issue 23, pp. 6535-6536, 2007.

\* cited by examiner

*Primary Examiner* — Jonathan S Lau

(57) ABSTRACT

An oligonucleotide derivative having the structure of formula (A) and methods for preparing the oligonucleotide derivative are disclosed. wherein $R^3$ is a first oligonucleotide; $R^1$ is selected from the group consisting of alkyl, cycloalkyl, aryl, heterocyclyl, heteroaryl, a polyethylene glycol, a peptide, a protein, a polysaccharide, and a second oligonucleotide; $R^2$ is a linker or a direct bond; $Z^1$ is $NR^4$, S, or O, and $Z^2$ is $NR^4$ or S, wherein $R^4$ is selected from H, alkyl, aryl, heterocyclyl, or heteroaryl. A method includes: synthesizing an oligonucleotide derivative comprising an amino or thiol group; and reacting a 3,4-dialkoxycyclobutene-1,2-dione with the oligonucleotide derivative to produce an oligonucleotide-squarate mono-conjugate.

17 Claims, 4 Drawing Sheets

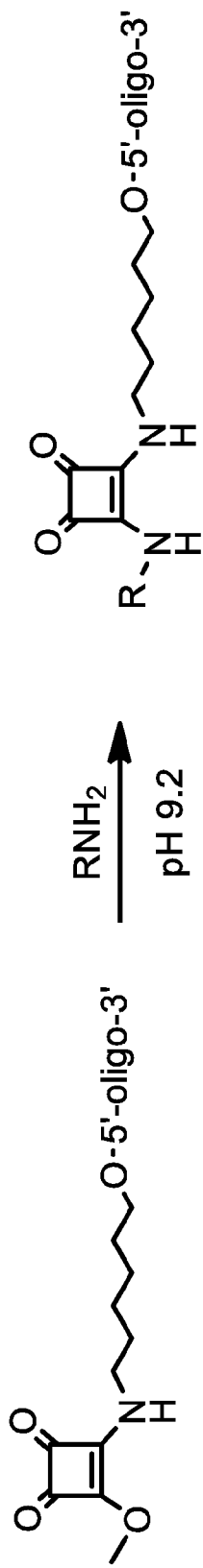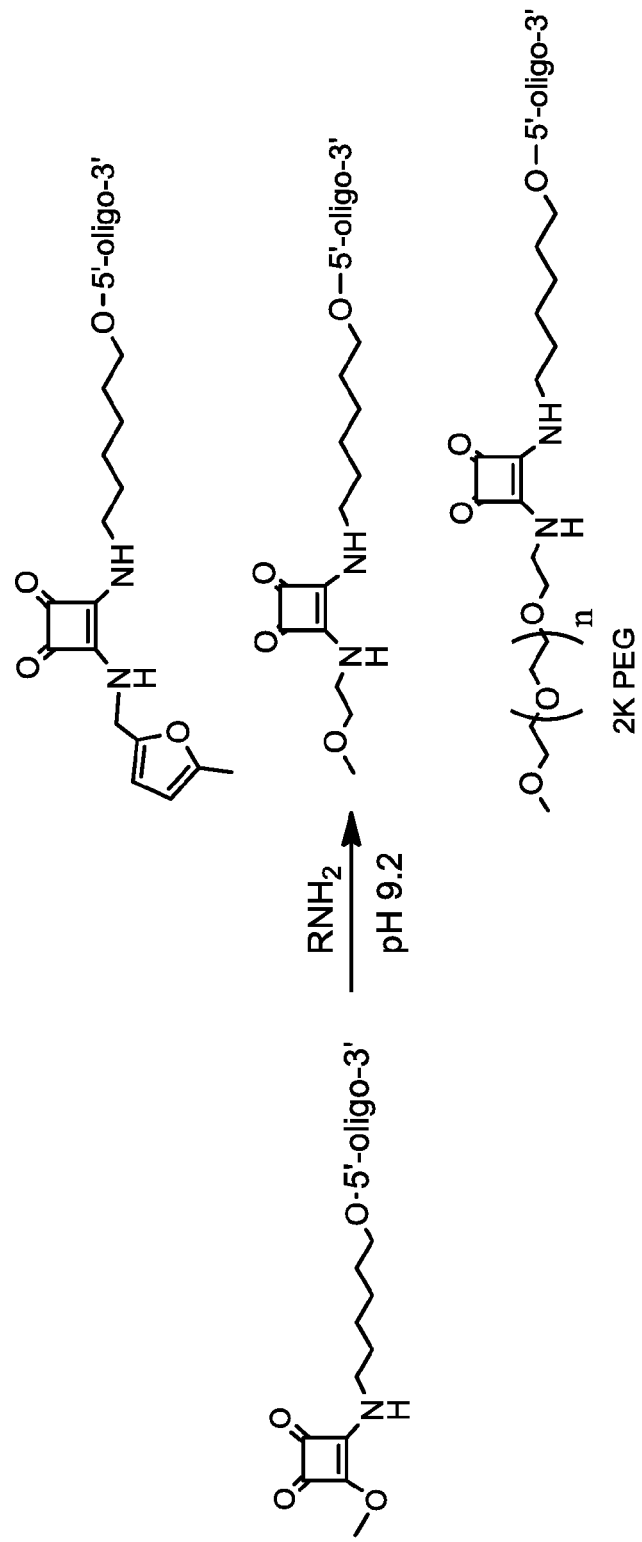
FIG. 3
FIG. 4

COMPOSITIONS AND METHODS FOR CONJUGATING OLIGONUCLEOTIDES

PRIORITY CLAIMS AND RELATED PATENT APPLICATIONS

This application claims the benefit of priority from U.S. Provisional Application Ser. No. 61/649,766, filed on May 21, 2012, the entire content of which is incorporated herein by reference in its entirety.

FIELD OF THE INVENTION

The present application relates generally to the field of reagents, synthesis and purification of oligonucleotides. More particularly, the invention relates to compositions of oligonucleotide derivatives and methods for conjugating oligonucleotides.

BACKGROUND OF THE INVENTION

Many methods are available for conjugating oligonucleotides with other molecules. These methods typically involve attachment of a reactive moiety on the target entity to be coupled with the oligonucleotide. The target entities with the reactive moieties are often made separately, usually by organic synthesis methods, and purified before use.

In each case the oligonucleotides are modified with appropriate functional groups for reacting with the reactive moieties on the target entities. Modifications of oligonucleotides are often accomplished by making special phosphoramidites and/or modified bases, and incorporating them into the oligonucleotide sequences at the desired points. Many of these amidite reagents contain functional groups that require protecting groups for the coupling of these reagents to the oligonucleotides. These protecting groups must be removed before the subsequent conjugation reaction occurs. Alternatively, the reactive moieties on the target entities may be created before the conjugation to the oligonucleotides.

Most of current coupling chemistries involve the use or creation of hydrolytically and/or oxidatively unstable species of at least one of the conjugation partners. This is a problem under conditions (typically in aqueous solutions) needed for conjugation with the oligonucleotides (or protein, or any organic insoluble/water soluble species). Newer conjugation chemistries may generate a novel structure upon reaction. For example, U.S. Pat. No. 6,737,236, issued to Pieken et al., discloses cycloaddition reactions for the conjugations of biomolecules. One example, a 1,3-dipolar cycloaddition conjugation between an alkyne and an azide (later labeled under the general term "Click" chemistry by Sharpless et. al. Angew. Chem. Int. Ed. 40: 2004 (2001) produces a substituted triazine as part of the conjugation product. These new chemical entities can be a problem if the oligonucleotide conjugates are used in humans because these new chemical entities may cause toxicity unrelated to the oligonucleotide products.

SUMMARY OF THE INVENTION

One aspect of the invention relates to oligonucleotide derivatives having the structure of formula (A):

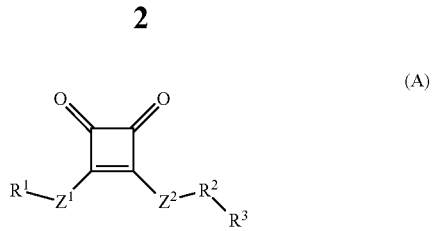

wherein $R^3$ is a first oligonucleotide; $R^1$ is selected from the group consisting of alkyl, cycloalkyl, aryl, heterocyclyl, heteroaryl, a polyethylene glycol, a peptide, a protein, a polysaccharide, and a second oligonucleotide; $R^2$ is a linker or a direct bond; $Z^1$ is $NR^4$, S, or O, and $Z^2$ is $NR^4$ or S, wherein $R^4$ is selected from H, alkyl, aryl, heterocyclyl, or heteroaryl.

In some embodiments of the invention, $R^2$ is a ($C_1$-$C_{12}$) linker attached to a 5' hydroxy group, a 3' hydroxy group, or an exocyclic amino group on a nucleobase of the first oligonucleotide. In some embodiments of the invention, $Z^2$ is NH. In some embodiments of the invention, $R^1$ is a ($C_1$-$C_{12}$) alkyl and $Z^1$ is O.

In some embodiments of the invention, $R^1$ is a 1K-40K polyethylene glycol and $Z^1$ is NH. In some embodiments of the invention, $R^1$ is a second oligonucleotide and $Z^1$ is NH, wherein the second oligonucleotide may be complementary to the first oligonucleotide.

Another aspect of the invention relates to methods for conjugating oligonucleotides. A method in accordance with one embodiment of the invention includes: synthesizing an oligonucleotide derivative comprising an amino or thiol group; and reacting a 3,4-dialkoxycyclobutene-1,2-dione with the oligonucleotide derivative to produce an oligonucleotide-squarate mono-conjugate.

In some embodiments of the invention, a method further comprises reacting the oligonucleotide-squarate mono-conjugate with a target entity selected from a polyethylene glycol, a peptide, a protein, a polysaccharide, or a second oligonucleotide.

In some embodiments of the invention, the oligonucleotide comprises a second amino or thiol group at a second location in the oligonucleotide derivative, the method further comprising forming an intra-oligonucleotide crosslink creating a cyclic structure.

Other aspects and advantages of the invention will be apparent from the following description and the appended claims.

BRIEF DESCRIPTION OF DRAWINGS

FIG. 3 shows conjugation of an oligonucleotide-squarate mono-adduct with a target entity (e.g., R—$NH_2$) in accordance with one embodiment of the invention.

FIG. 4 shows conjugation of an oligonucleotide-squarate mono-adduct with various target entities in accordance with embodiments of the invention.

DEFINITIONS

Figure 1:
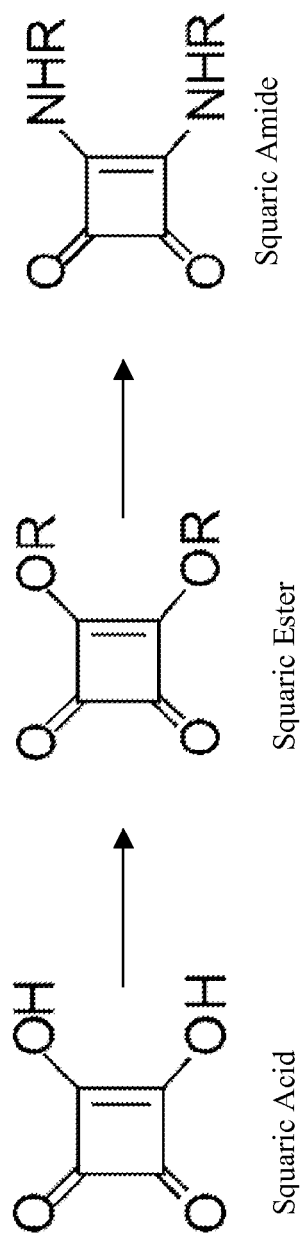
FIG. 1 shows squaric acid and various reactions with the squaric acid.

Unless defined otherwise, all technical and scientific terms used herein have the same meaning as commonly understood by one of ordinary skill in the art to which this invention belongs. Terms and symbols of nucleic acid chemistry, biochemistry, genetics, and molecular biology used herein follow those of standard treatises and texts in the field, e.g. Kornberg and Baker, DNA Replication, Second Edition (W.H. Freeman, New York, 1992); Lehninger, Biochemistry, Second Edition (Worth Publishers, New York, 1975); Strachan and Read, Human Molecular Genetics, Second Edition (Wiley-Liss, New York, 1999); Eckstein, editor, Oligonucleotides and Analogs: A Practical Approach (Oxford University Press, New York, 1991); Gait, editor, Oligonucleotide Synthesis: A Practical Approach (IRL Press, Oxford, 1984); Sambrook et al., Molecular Cloning: A Laboratory Manual, 2.sup.nd Edition (Cold Spring Harbor Laboratory, 1989); and the like. Still, certain terms are defined below for the sake of clarity and ease of reference.

The term "nucleoside", as used herein, refers a modified or naturally occurring deoxyribonucleoside or ribonucleoside or any chemical modifications thereof. Modifications of the nucleosides include, but are not limited to, 2'-, 3'- and 5'-position sugar modifications, 5- and 6-position pyrimidine modifications, 2-, 6- and 8-position purine modifications, modifications at exocyclic amines, substitution of 5-bromo-uracil, and the like. Nucleosides can be suitably protected and derivatized to enable oligonucleotide synthesis by methods known in the field, such as solid phase automated synthesis using nucleoside phosphoramidite monomers, H-phosphonate coupling or phosphate triester coupling.

The term "nucleotide", as used herein, refers to a modified or naturally occurring deoxyribonucleotide or ribonucleotide. Nucleotide is a nucleoside as defined above having one or several phosphates or substituted phosphates attached at the 5'-, 2'- or 3'-positions. Nucleotides typically include purines and pyrimidines, which include thymidine, cytidine, guanosine, adenine and uridine.

The term "oligonucleotide", as used herein, refers to a polynucleotide formed from a plurality of linked nucleotide units as defined above. The nucleotide units each include a nucleoside unit linked together via a phosphate linking group. The term oligonucleotide also refers to a plurality of nucleotides that are linked together via linkages other than phosphate linkages such as phosphorothioate linkages. The oligonucleotide may be naturally occurring or non-naturally occurring. In a preferred embodiment the oligonucleotides of this invention have between 1-1,000 nucleotides. Oligonucleotides may be synthetic or may be made enzymatically, and, in some embodiments, are 10 to 50 nucleotides in length. Oligonucleotides may include ribonucleotide monomers (i.e., may be oligoribonucleotides) or deoxyribonucleotide monomers. Oligonucleotides may be 10 to 20, 21 to 30, 31 to 40, 41 to 50, 51-60, 61 to 70, 71 to 80, 80 to 100, 100 to 150, 150 to 200, 200 to 500, or greater than 500 nucleotides in length, for example.

The term "alkyl", as used herein, refers to a saturated straight chain, branched or cyclic hydrocarbon group of 1 to 24 (i.e., ($C_1$-$C_{24}$)alkyl), typically 1-12 (i.e., ($C_1$-$C_{12}$)alkyl) carbon atoms, more typically 1-6 carbon atoms (i.e., ($C_1$-$C_6$)alkyl), such as methyl, ethyl, n-propyl, isopropyl, n-butyl, isobutyl, t-butyl, pentyl, cyclopentyl, isopentyl, neopentyl, hexyl, isohexyl, cyclohexyl, 3-methylpentyl, 2,2-dimethylbutyl, and 2,3-dimethylbutyl. The term "lower alkyl" intends an alkyl group of one to six carbon atoms, and includes, for example, methyl, ethyl, n-propyl, isopropyl, n-butyl, isobutyl, t-butyl, pentyl, cyclopentyl, isopentyl, neopentyl, hexyl, isohexyl, cyclohexyl, 3-methylpentyl, 2,2-dimethylbutyl, and 2,3-dimethylbutyl. The term "cycloalkyl" refers to cyclic alkyl groups such as cyclopropyl, cyclobutyl, cyclopentyl, cyclohexyl, cycloheptyl and cyclooctyl.

"Alkylene" and "alkylene chain", as used herein, refer to a straight or branched divalent hydrocarbon chain, linking the rest of the molecule to a radical group, consisting solely of carbon and hydrogen, containing no unsaturation and having from one to twelve carbon atoms, preferably having from one to eight carbons, e.g., methylene, ethylene, propylene, n-butylene, and the like. The alkylene chain may be attached to the rest of the molecule and to the radical group through one carbon within the chain or through any two carbons within the chain.

Moreover, the term "alkyl" includes "modified alkyl", which references an alkyl group having from one to twenty-four (C1-C20) carbon atoms, and further having additional groups, such as one or more linkages selected from ether-, thio-, amino-, phospho-, oxo-, ester-, and amido-, and/or being substituted with one or more additional groups including lower alkyl, aryl, alkoxy, thioalkyl, hydroxyl, amino, sulfonyl, thio, mercapto, imino, halo, cyano, nitro, nitroso, azide, carboxy, sulfide, sulfone, sulfoxy, phosphoryl, silyl, silyloxy, and boronyl.

Similarly, the term "lower alkyl" includes "modified lower alkyl", which references a group having from one to eight carbon atoms and further having additional groups, such as one or more linkages selected from ether-, thio-, amino-, phospho-, keto-, ester-, and amido-, and/or being substituted with one or more groups including lower alkyl; aryl, alkoxy, thioalkyl, hydroxyl, amino, sulfonyl, thio, mercapto, imino, halo, cyano, nitro, nitroso, azide, carboxy, sulfide, sulfone, sulfoxy, phosphoryl, silyl, silyloxy, and boronyl. The term "alkoxy" as used herein refers to a substituent —O—R wherein R is alkyl as defined above. The term "lower alkoxy" refers to such a group wherein R is lower alkyl. The term "thioalkyl" as used herein refers to a substituent —S—R wherein R is alkyl as defined above.

The term "aryl", as used herein, refers to aromatic monocyclic or multicyclic, some of which may be fused together, hydrocarbon ring system consisting only of hydrogen and carbon and containing from 6 to 19 carbon atoms (represented as ($C_6$-$C_{19}$)aryl), preferably 6 to 10 carbon atoms (represented as ($C_6$-$C_{10}$)aryl), where the ring system may be partially or fully saturated. Aryl groups include, but are not limited to groups such as fluorenyl, phenyl and naphthyl. Unless stated otherwise specifically in the specification, the term "aryl" is meant to include aryl radicals optionally substituted by one or more substituents selected from ($C_1$-$C_{12}$)hydrocarbyl, —O—R", —O—CO—R", —CO—O—R", —NR'—R", —NR'—CO—R", —CO—NR'—R", —CO—R", —R—O—R", —R—O—CO—R", —R—CO—O—R", —R—NR'—R", —R—NR'—CO—R", —R—CO—NR'—R", —R—CO—R", —CN, halogen, or a combination thereof, wherein R' and R" are independently H or ($C_1$-$C_{12}$)hydrocarbyl, and R is ($C_1$-$C_{12}$)hydrocarbyl.

The term "heteroaryl", as used herein, refers to a 5- to 18-membered monocyclic- or bicyclic- or fused polycyclic-ring system which consists of carbon atoms and from one to five heteroatoms selected from the group consisting of nitrogen, oxygen and sulfur. Preferably heteroaryl is a 5- to 12- or 5- to 9-membered ring system. For purposes of this invention, the heteroaryl radical may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Examples include, but are not limited to, azepinyl, acridinyl, benzimidazolyl, benzthiazolyl, benzindolyl, benzothiadiazolyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, furanyl, furanonyl, isothiazolyl, imidazolyl, indolyl, indazolyl, isoindolyl, indolinyl, isoindolinyl, indolizinyl, isoxazolyl, naphthyridinyl, oxadiazolyl, 2-oxoazepinyl, oxazolyl, oxiranyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, thiazolyl, thiadiazolyl, triazolyl, tetrazolyl, triazinyl, and thiophenyl. Unless stated otherwise specifically in the specification, the term "heteroaryl" is meant to include heteroaryl radicals as defined above which are optionally substituted by one or more substituents selected from $(C_1$-$C_{12})$hydrocarbyl, —O—R", —O—CO—R", —CO—O—R", —NR'—R", —NR'—CO—R", —CO—R", —CO—NR'—R", —CO—R", —R—O—R", —R—O—CO—R", —R—CO—O—R", —R—NR'—R", —R—NR'—CO—R", —R—CO—NR'—R", —R—CO—R", —CN, halogen, or a combination thereof, wherein R' and R" are independently H or $(C_1$-$C_{12})$hydrocarbyl, and R is $(C_1$-$C_{12})$hydrocarbyl.

The term "heteroaryl" also refers to a group in which a heteroaromatic ring is fused to one or more aryl, cycloaliphatic, or heterocyclyl rings, where the radical or point of attachment is on the heteroaromatic ring. Nonlimiting examples include but are not limited to 1-, 2-, 3-, 5-, 6-, 7-, or 8-indolizinyl, 1-, 3-, 4-, 5-, 6-, or 7-isoindolyl, 2-, 3-, 4-, 5-, 6-, or 7-indolyl, 2-, 3-, 4-, 5-, 6-, or 7-indazolyl, 2-, 4-, 5-, 6-, 7-, or 8-purinyl, 1-, 2-, 3-, 4-, 6-, 7-, 8-, or 9-quinolizinyl, 2-, 3-, 4-, 5-, 6-, 7-, or 8-quinoliyl, 1-, 3-, 4-, 5-, 6-, 7-, or 8-isoquinoliyl, 1-, 4-, 5-, 6-, 7-, or 8-phthalazinyl, 2-, 3-, 4-, 5-, or 6-naphthyridinyl, 2-, 3-, 5-, 6-, 7-, or 8-quinazolinyl, 3-, 4-, 5-, 6-, 7-, or 8-cinnolinyl, 2-, 4-, 6-, or 7-pteridinyl, 1-, 2-, 3-, 4-, 5-, 6-, 7-, or 8-4aH carbazolyl, 1-, 2-, 3-, 4-, 5-, 6-, 7-, or 8-carbzaolyl, 1-, 3-, 4-, 5-, 6-, 7-, 8-, or 9-carbolinyl, 1-, 2-, 3-, 4-, 6-, 7-, 8-, 9-, or 10-phenanthridinyl, 1-, 2-, 3-, 4-, 5-, 6-, 7-, 8-, or 9-acridinyl, 1-, 2-, 4-, 5-, 6-, 7-, 8-, or 9-perimidinyl, 2-, 3-, 4-, 5-, 6-, 8-, 9-, or 10-phenathrolinyl, 1-, 2-, 3-, 4-, 6-, 7-, 8-, or 9-phenazinyl, 1-, 2-, 3-, 4-, 6-, 7-, 8-, 9-, or 10-phenothiazinyl, 1-, 2-, 3-, 4-, 6-, 7-, 8-, 9-, or 10-phenoxazinyl, 2-, 3-, 4-, 5-, 6-, or 1-, 3-, 4-, 5-, 6-, 7-, 8-, 9-, or 10-benzisoqinolinyl, 2-, 3-, 4-, or thieno[2,3-b]furanyl, 2-, 3-, 5-, 6-, 7-, 8-, 9-, 10-, or 11-7H-pyrazino[2,3-c]carbazolyl, 2-, 3-, 5-, 6-, or 7-2H-furo[3,2-b]-pyranyl, 2-, 3-, 4-, 5-, 7-, or 8-5H-pyrido[2,3-d]-o-oxazinyl, 1-, 3-, or 5-1H-pyrazolo[4,3-d]-oxazolyl, 2-, 4-, or 54H-imidazo[4,5-d]thiazolyl, 3-, 5-, or 8-pyrazino[2,3-d]pyridazinyl, 2-, 3-, 5-, or 6-imidazo[2,1-b]thiazolyl, 1-, 3-, 6-, 7-, 8-, or 9-furo[3,4-c]cinnolinyl, 1-, 2-, 3-, 4-, 5-, 6-, 8-, 9-, 10, or 11-4H-pyrido[2,3-c]carbazolyl, 2-, 3-, 6-, or 7-imidazo[1,2-b][1,2,4]triazinyl, 7-benzo[b]thienyl, 2-, 4-, 5-, 6-, or 7-benzoxazolyl, 2-, 4-, 5-, 6-, or 7-benzimidazolyl, 2-, 4-, 4-, 5-, 6-, or 7-benzothiazolyl 1-, 2-, 4-, 5-, 6-, 7-, 8-, or 9-benzoxapinyl, 2-, 4-, 5-, 6-, 7-, or 8-benzoxazinyl, 1-, 2-, 3-, 5-, 6-, 7-, 8-, 9-, 10-, or 11-1H-pyrrolo[1,2-b][2]benzazapinyl. Typical fused heteoary groups include, but are not limited to 2-, 3-, 4-, 5-, 6-, 7-, or 8-quinolinyl, 1-, 3-, 4-, 5-, 6-, 7-, or 8-isoquinolinyl, 2-, 3-, 4-, 5-, 6-, or 7-indolyl, 2-, 3-, 4-, 5-, 6-, or 7-benzo[b]thienyl, 2-, 4-, 5-, 6-, or 7-benzoxazolyl, 2-, 4-, 5-, 6-, or 7-benzimidazolyl, 2-, 4-, 5-, 6-, or 7-benzothiazolyl.

The term "cycloalkyl", as used herein, refers to a stable non-aromatic monocyclic or bicyclic hydrocarbon radical consisting solely of carbon and hydrogen atoms, having from three to fifteen carbon atoms, preferably having from three to twelve carbon atoms, $(C_3$-$C_{12})$cycloalkyl, and which is saturated or unsaturated and attached to the rest of the molecule by a single bond, e.g., cyclopropyl, cyclobutyl, cyclopentyl, cyclohexyl, decalinyl and the like. Unless otherwise stated specifically in the specification, the term "cycloalkyl" is meant to include cycloalkyl radicals which are optionally substituted by one or more substituents selected from —O—R", —O—CO—R", —CO—O—R", —NR'—R", —NR'—CO—R", —CO—NR'—R", —CO—R", —CN, halogen, or a combination thereof, wherein R' and R" are independently H or $(C_1$-$C_{12})$hydrocarbyl.

The terms "heterocyclyl" or "heterocycle", as used herein, refer to an optionally substituted, saturated or partially unsaturated, nonaromatic cyclic group, e.g., which is a 4- to 7-membered monocyclic, 7- to 12-membered bicyclic or 10- to 15-membered tricyclic ring system, which has at least one heteroatom in at least one carbon atom-containing ring. Each ring of the heterocyclic group containing a heteroatom may have 1, 2, 3, or 4 heteroatoms selected from nitrogen atoms, oxygen atoms and sulfur atoms, wherein the nitrogen and sulfur heteroatoms may also optionally be oxidized. The heterocyclic group may be attached at a heteroatom or a carbon atom. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. The bicyciic and tricyclic heterocyclyl groups can be fused or spiro rings or ring groups. Preferably heterocyclyl is a 4- to 12-membered ring system. Also preferably heterocyclyl is a 4- to 9-membered ring system.

Exemplary monocyclic heterocyclic groups include oxetanyl, thiatanyl, azetidinyl, dihydrofuranyl, tetrahydrofuranyl, dihydrothiophenyl, tetrahydrothiophenyl, pyrrolidinyl, dihydropyrazolyl, tetrahydropyrazolyl, dihydropyridinyl, tetrahydropyridinyl, dihydrothiopyranyl, tetrahydrothipyranyl, pyranyl, dihydropyranyl, tetrahydropyranyl, thiopyranyl, dihydrothiopyranyl, tetrahydrothiopyranyl, ptperidinyl, piperazinyl, morphoiinyl, azepinyl, dihydroazepinyl, tetrahydroazepinyl, 2-oxopiperazinyl, 2-oxopiperidinyl, 2-oxopyrrolodinyl, 2-oxoazepinyl, oxepanyl, thiepanyl, dihyrothiepinyl, tetrahydrothiepinyl, dihydrooxepinyl, tetrahydrooxepinyl, 1,4-dioxanyl, 1,4-oxathianyl, morphoiinyl, oxazolyl, oxazolidinyl, isoxazolinyi, A-ptperidony!, isoxazoiinyi, isoxazolyl, 1,4-azathianyl, 1,4-oxathiepanyl, 1,4-oxaazepanyl, 1,4-dithiepanyl, 1,4-thieaxepanyl, 1,4-diazepanyl, tropanyl, 3,4-dihydro-2H-pyranyl, 5,6-dihydro-2H-pyranyl, thiazolidinyl, thiamorpholinyl, thiamorpholinyl sulfoxide, thiamorphoiinyl suifone, 1,3-dioxolane and tetrahydro-1,1-dioxothienyl, 1,1,4-trioxo-1,2,5-thiadiazolidin-2-yl, pyrazolinyl, and the like.

Exemplary bicyclic heterocyclic groups include but are not limited to, dihydroindolyl, quinuctidinyl, tetrahydroquinolinyl, decahydroquinolinyl, 2-oxa-6-azaspiro[3,3]heptan-6-yl, tetrahydroisoquinoiinyl, decahydroisoquinoiinyl, dihydroisoindolyl, indoiinyl, norboranyl, adamantanyl, and the like.

Unless stated otherwise specifically in the specification, the term "heterocyclyl" is meant to include heterocyclyl radicals as defined above which are optionally substituted by one or more substituents selected from —O—R", —O—CO—R", —CO—O—R", —NR'—R", —NR'—CO—R", —CO—NR'—R", —CO—R", —CN, halogen, or a combination thereof, wherein R' and R" are independently H or $(C_1-C_{12})$hydrocarbyl.

The term "direct bond", as used herein, means that the two entities linked by the "direct bond" are connected to each other directly. The direct bond may be a single bond or a double bond, for example.

The term "DNA", or "deoxyribonucleic acid", as used herein, refers to a polynucleotide or oligonucleotide that comprises at least one deoxyribonucleotide residue.

The term "RNA", or "ribonucleic acid", as used herein, refers to a polynucleotide or oligonucleotide that comprises at least one ribonucleotide residue.

As used herein, a "linker" bridges two moieties in a molecule. A "linker" may be a hydrocarbyl chain (e.g., $(C_1-C_{12})$alkylene, $(C_2-C_{12})$alkenylene), optionally substituted with a substituent group, or a linker may be a hydrocarbyl chain interspersed with other atoms, as represented by —(CHR')$_a$—W$_b$—(CHR')$_c$—V$_d$—(CHR')$_e$—, wherein W and V are independently —O—, —S—, or —NR—; R' is H or $(C_1-C_6)$alkyl; and a, b, c, d, and e are independently an integer from 0 to 10, preferably from 0 to 6, or preferably from 0 to 3, and the sum of a, b, c, d, and e is preferably an integer from 2 to 6. The optional substituent group may be —O—R", —O—CO—R", —NR'—R", —NR'—CO—R", —CO—NR'—R", —CO—R", —CN, halogen, or a combination thereof, wherein R' and R" are independently H or $(C_1-C_6)$ hydrocarbyl.

The term "polyethylene glycol", as used herein, refers to polyether compounds having a formula R—(O—CH$_2$—CH$_2$)$_n$—O—R', wherein R and R' are independently H or an alkyl. "Polyethylene glycol derivative" refers to polyether compounds having a formula R—(O—CH$_2$—CH$_2$)$_n$—X—R', wherein R and R' are independently H or an alkyl, and X is O or NH.

The term "polypeptide", as used herein, refers a molecule containing a plurality of amino acids linked by peptide bonds. A polypeptide may be generated from a natural protein or chemically synthesized.

The term "protein", as used herein, refers to a molecule containing one or more polypeptides. A protein is often of natural origin, but may include those modified from a natural protein.

The terms "polysaccharide" or "polycarbohydrate", as used herein, refer to a carbohydrate molecule having a plurality of sugar moieties linked by glycosidic bonds.

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present, and, thus, the description includes structures wherein a non-hydrogen substituent is present and structures wherein a non-hydrogen substituent is not present.

DETAILED DESCRIPTION OF THE INVENTION

Embodiments of the invention relate to methods for conjugating oligonucleotides with other molecules or target entities. The oligonucleotides may include DNA, RNA, or a chimeric DNA/RNA. The target entities may be any desired targets, such as other oligonucleotides, proteins/peptides, carbohydrates, or supports (which may include soluble polymers or solid supports, such as resins, glass beads, magnetic beads, matrix surfaces, etc.).

Embodiments of the invention are based on the fact that squaric acid and derivatives thereof can be readily coupled with amino groups under mild conditions. These conjugation processes provide simple aqueous based methods for producing oligonucleotide conjugates. The products from these reactions are stable and can be readily isolated and stored. In addition, squaric acid derivatives have been used in modifications of pharmaceuticals and are found to be nontoxic.

FIG. 1 shows the structure of squaric acid (i.e., cyclobutene 3,4 dione), which can be reacted with alcohols to give squaric diesters. The esterification can easily occur in the presence of an acid catalyst, as in the usual esterification of carboxylic acids. Nucleophilic substitution of the squaric acid esters can readily occur, e.g., with amines as nucleophiles to give the corresponding monoamides or diamides. These properties can be used in many applications, including modification of biological molecules to change their properties.

In addition to the esters, other squaric acid derivatives that can also be used to react with nucleophiles (e.g., amino groups or thiol groups) include squaric halides, squaric ester halide, and squaric imidazoles. All these squaric acid derivatives may be used with embodiments of the invention, and all these reagents can react with oligonucleotides having amino or thiol functional groups. Embodiments of the invention preferably use squaric acid diesters as the reagents.

The use of squaric acid derivatives has been described for conjugations with small molecules, and for conjugation of small molecules to proteins or carbohydrates. It has also been used to couple large molecules, such as a 20K polysaccharide to a protein. In addition, U.S. Pat. No. 6,602,692, issued to Gliisenkamp et al., discloses the use of squaric acid derivatives to conjugate peptides to solid support that has been modified with a squaric derivative. The disclosure of the '692 patent is incorporated by reference in its entirety.

Embodiments of the invention may use any of the above squaric acid derivatives. Preferred embodiments of the invention use squaric acid esters, which may be referred generally as squarate. The squaric acid esters are diesters, wherein the two ester groups (—OR groups) maybe the same or different.

While the uses of squarate to conjugate various molecules are known, no applications using this technology for conjugations to DNA or RNA have been reported. Considerable efforts have been directed to the application of oligonucleotides and oligonucleotide analogs as diagnostic/research reagents or as potential therapeutics. Examples of potential applications of oligonucleotides as pharmaceutics may include antisense oligonucleotides that can bind to certain coding regions to prevent the expression of proteins or to block various cell functions. Furthermore, the development of SELEX techniques (Systematic Evolution of Ligands by Exponential Enrichment) (Tuerk and Gold, Science, 249: 505 (1990)) makes it possible to identify oligonucleotides that will bind to almost any biologically interesting targets.

The potential uses of oligonucleotides as pharmaceutical agents have led to further development of various chemical modifications aiming to increase their therapeutic activities and stabilities. Such modifications may increase cell penetration of the oligonucleotides or their resistance to nucleases. In addition, these modifications may enhance the bindings of oligonucleotides to their targets or may improve the pharmacokinetic properties of the oligonucleotides.

Therefore, methods that can easily modify oligonucleotides for various applications are desirable.

Embodiments of the invention provide methods for the modifications of oligonucleotides under very mild conditions and they methods are suitable for applications in the modifications of oligonucleotide pharmaceuticals. In accordance with embodiments of the invention, oligonucleotide derivatives (containing reactive functional groups for coupling with squaric acid derivatives) may be prepared with any suitable methods. For example, the oligonucleotides may be synthesized with a reactive functional group (e.g., an amino group) for coupling with a squaric acid derivative. The reactive functional groups, for example, may be an amino group or a thiol group.

Various methods for attaching functional groups to oligonucleotides are known. (For a review, see Goodchild, Bioconjugate Chemistry, 1:165-187 (1990)). Once the chemically reactive functional groups are attached to oligonucleotides (e.g., at the 5'- and or 3'terminus), these reactive functional groups can be used to couple with various conjugates. For example, a primary aliphatic amino group may be incorporated at the 5'-terminus of the oligonucleotide in the final step of the synthesis of an oligonucleotide. Reagents for linking to the 5' terminus of an oligonucleotide are commercially available. For example, various linkers having different lengths of —(CH$_2$)$_n$— connectors for linking to the 5' terminus of an oligonucleotide are available. One example is 5'-Amino-Modifier C6 is available from Glen Research Corp. (Sterling, Va.). Amino modifiers for the 3' end of oligonucleotides are also readily available, either as phosphoramidites or already attached to the synthesis solid support.

The reagents used to modify the oligonucleotides to provide reactive functional groups may be in the form of phosphoramidites, which may be coupled to the free 5'-hydroxyl group of the full length oligonucleotide while it is attached to a solid support. This coupling would be like attaching another nucleotide monomer. (See, e.g., Theison et al., Tetrahedron Lett., 33:5033-5036 (1992).)

In accordance with some embodiments of the invention, the reactive groups (e.g., amino or thiol groups) may be attached to the oligonucleotides using modified nucleotides. In this case, the reactive groups need not be attached to the 5' or 3' end. Instead, one can use these modified nucleotide analogs to incorporate the reactive groups at the internal positions. Some examples of such modified nucleotides are shown below:

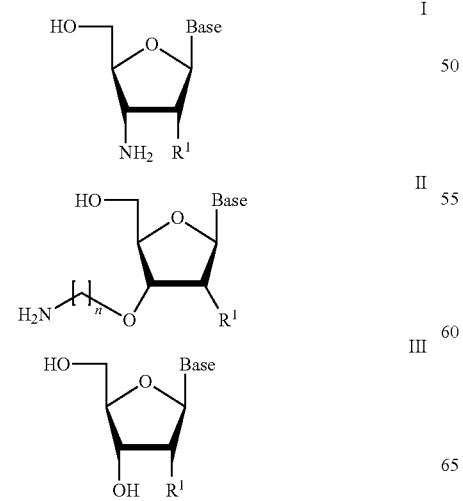

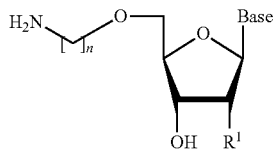

In the above examples, R$_1$ is H or OH. Formula (I) represents a natural nucleoside or deoxynucleoside (R is H or OH), and formulae (II)-(IV) (wherein n is an integer greater than 0) represent various analogs having reactive amino groups modifications on the sugar rings. These amino groups will be protected during incorporation of these analogs into oligonucleotides. Some of these reagents are commercially available or may be prepared according to procedures known in the art.

Other modified nucleotide analogs may have modifications on the purine or pyrimidine rings, such as those shown below:

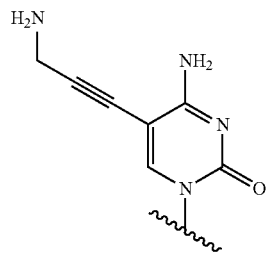

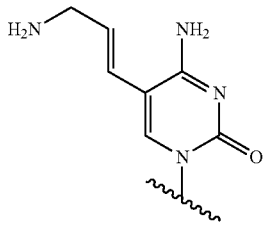

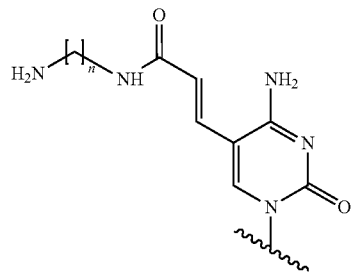

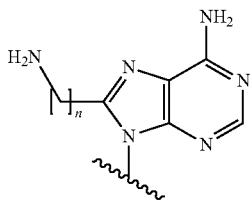

-continued

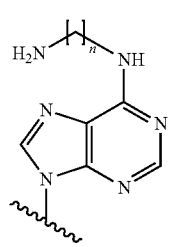

IX

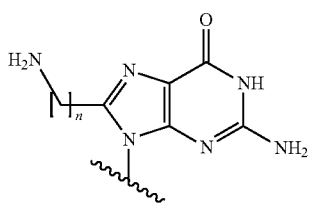

X

The above formulae (V)-(X) (wherein n is an integer greater than 0) show examples of nucleotide analogs that contain reactive amino groups. These analogs may be used to incorporate into oligonucleotides after these amino groups have been protected. Some of these reagents are commercially available or may be prepared according to procedures known in the art.

Once the oligonucleotides are derivatized with reactive functional groups (e.g., amino or thiol groups), they may be used to couple with squaric acid derivatives. The following examples illustrate some embodiments of the invention.

In accordance with some embodiments of the invention, the oligonucleotide-squarate mono conjugates could be used to attach oligonucleotides to other target entities, such as peptides, proteins, oligosaccharides, solid surfaces, polymeric materials, nanoparticles, hydrogels, and small molecules.

In accordance with some embodiments of the invention, these mono conjugates can be used to couple with other handles that may be selected for particular purposes. One example of such application is to attach a diene moiety (e.g., a furan) to a oligonucleotide-squarate mono adduct in order for this to participate in a Diels Alder reaction with a dienophile-linked molecule (e.g., N-ethyl maleimide), which is disclosed in a co-pending application filed on the same day.

It should be noted that while examples described herein use amino groups to conjugate with a squarate, other nucleophilic groups (e.g., thiol) may also be used.

Treatment of the oligonucleotide mono squarate with limited amounts of species containing more than one amine (eq. di amines, tri amines, to polyamines) would provide a means to make mutimeric oligonucleotide structures.

Another application of this conjugation may be the coupling of two amino labeled oligonucleotides together to form cyclical or hairpin-type oligonucleotide structures. The oligonucleotides could be complimentary sequences, with a 3' amino label on one strand and a 5' amino label on the other. This would form a hairpin like dimer.

Advantages of the invention may include one or more of the following. Embodiments of the invention provide easy and efficient methods for the conjugation of oligonucleotides to various target entities. The reactions with squarates can be conducted in aqueous solutions with high yields and the products can be easily purified (e.g., by ultra filtration or by size exclusion chromatography). The mono-squarate adducts are stable and can be purified and stored for later uses.

The stability of the mono conjugate with DNA/RNA might allow coupling of a second amino labeled oligonucleotide that is not complementary to the sequence of the oligonucleotide-mono squarate species. The coupling of two non-complimentary oligonucleotides is very difficult to do non-enzymatically. Methods of the invention would provide access to these molecules. The squaric acid derivatives are small and would not illicit immunogenic responses, resulting in fewer adverse reactions when incorporating the functionality into pharmaceuticals.

EXAMPLES

Synthesis of Oligonucleotide-Squarate Mono Conjugate

An oligonucleotide is synthesized with an amino linker attached, using any method know in the art (see the above discussion). The example shown in FIG. 2 uses a TFA-protected amine C6 linker phosphoramidite (i.e., $CF_3$—CO—NH—$(CH_2)_6$—O—P$((O$—CH$(CH_3)_2)_2(O$—$CH_2$—$CH_2$—CN), which is coupled to the 5'-OH end of the oligonucleotide on solid support using the appropriate synthesis conditions. This coupling may be carried out under conditions similar to the coupling of a nucleotide monomer and can be performed while the oligonucleotide is still attached to a solid support. After the synthesis and deprotection as usual (standard ammonia and TEA 3HF for RNA), the mixture may be ultrafiltered against NaCl to remove all ammonia and ammonium salts. Finally, the retentate is washed with water to remove all excess salts. The oligonucleotide solution may then be concentrated down. The concentrate may be lyophilized or used as is.

Figure 2:
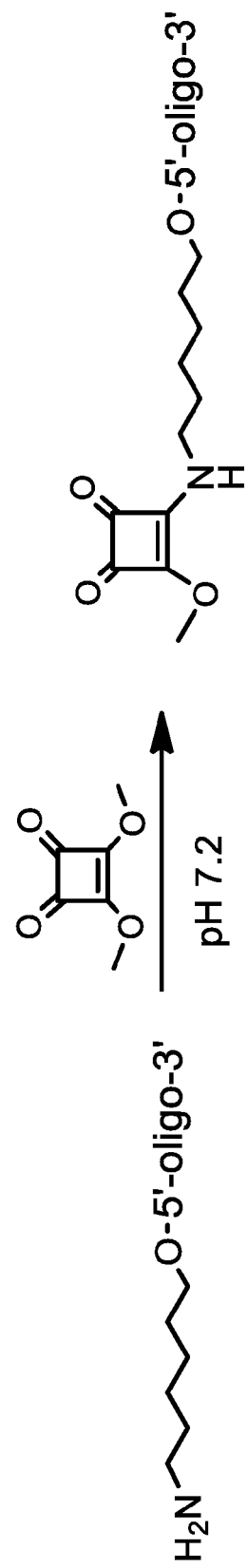
FIG. 2 shows a reaction between a modified oligonucleotide and a squaric acid diester in accordance with one embodiment of the invention.

Once the amino-labeled oligonucleotide is available, it can be coupled to a squaric acid derivative. For example, a solution of amino-labeled oligonucleotide, approximately 10 mg in 500 µL of 300 mM sodium phosphate, pH 7-8 was prepared. To this was added an excess of dimethyl ester of squaric acid (dimethyoxy cyclobutene 1,2 dione; approx. 0.75 mg to each mg of oligonucleotide), as shown in FIG. 2. Excess squaric ester is used to favor the formation of mono-substituted squarate derivative and to suppress the formation of di-substituted squarate derivatives.

The reaction mixture was kept at 25° C. and the pH of the solution was adjusted with dibasic phosphate to maintain the reaction pH between 7 and 7.8, as the pH tends to drop during conjugation. After about 4 hours, the reaction solution was filtered and washed with water in a 3K ultrafiltration (UF) spin cartridge to remove remaining small molecules. (e.g., excess squaric ester and salts). The UF retentate was lyophilized and analyzed by LCMS, which confirmed the formation of the desired product—i.e., an oligonucleotide-squarate mono adduct. Such adducts are very stable. For example, these mono substituted squarates are found to be stable for at least two days in aqueous solutions at pH=7, and for over 1 year at 4° C. as a lyophilized solid.

Alternatively, the reaction solution may be filtered and washed with water, followed by washing with a borate buffer, which may be used as the buffer for the next reaction and used directly in the next conjugation step (e.g., conjugation to a target entity shown below).

The above described coupling reaction is very efficient. The reactions have been run many times and these reactions are found to proceed to 90-99% completion, as judged by the amount of starting amino labeled oligonucleotides remaining after the conjugation. The reactions can be easily monitored by LCMS analysis.

Reaction of Oligonucleotide-Squarate Mono Conjugate with a Target Entity

The lyophilized squarate mono conjugate was taken up in a 25 mM sodium borate buffer, pH=9.2, and treated with an excess (e.g., 10-40 folds) of a target entity containing an amino group (e.g., NH$_2$—R) dissolved in a small amount of DMSO, as shown in FIG. 3. The mono conjugate pre-ultrafiltered in 25 mM borate buffer (see above) could be treated directly with the amine/DMSO mixture, without lyophilization and re-dissolution.

In this particular example, the target entity is a 5-methyl furfuryl amine (i.e., R=5-methyl-furfuryl). The reaction was run at room temperature for 2 hours. The reaction mixture was again concentrated and washed in the 3K UF spin cartridges to remove excess amine and salts. The retentate was lyophilized and a portion of the solid analyzed by LCMS, which showed the desired conjugate was formed in approximately 95% yield, based on starting mono conjugate.

Based on these protocols, various target entities have been conjugated with oligonucleotides. Some examples of these conjugations are shown in FIG. 4. The preparations of PEG-oligonucleotide conjugates are known, see e.g., Goodchild et al., Bioconjugate Chem., 1:165 (1990); and Zalipsky et al., Bioconjugate Chem., 6:150 (1995). The PEG conjugates can be used to improve the in vivo stabilities of the oligonucleotides and/or to reduce the immunogeneities of the oligonucleotides.

Formation of Oligonucleotide Duplex with Two Complimentary Oligonucleotides

An RNA 20 mer that contained a 5' Hexaethylene glycol (HEG) spacer linker followed by the standard six carbon amino linker was made using standard oligonucleotide solid phase synthesis techniques. The HEG and C6 amino linkers (both are commercially available) were added as phosphoramidites using standard oligonucleotide synthesis/deprotection protocols, see example 1 above. The crude RNA was purified by anion exchange chromatography and ultrafiltered on a 2K Hydrosart membrane prior to lyophilization. LCMS analysis of the lyophilized material gave the expected molecular weight of the modified oligonucleotide. 150 mg of this lyophilized amino modified RNA was taken up in 3.0 mL of sodium phosphate giving a solution with a pH range of 7-8. To this solution was added 100 mg of dimethoxy squarate dissolved in 300 uL of DMSO. LCMS analysis after 1 hour showed that the amino labeled RNA had been converted completely over to the desired mono squarate, as shown in FIG. 5.

Figure 5:
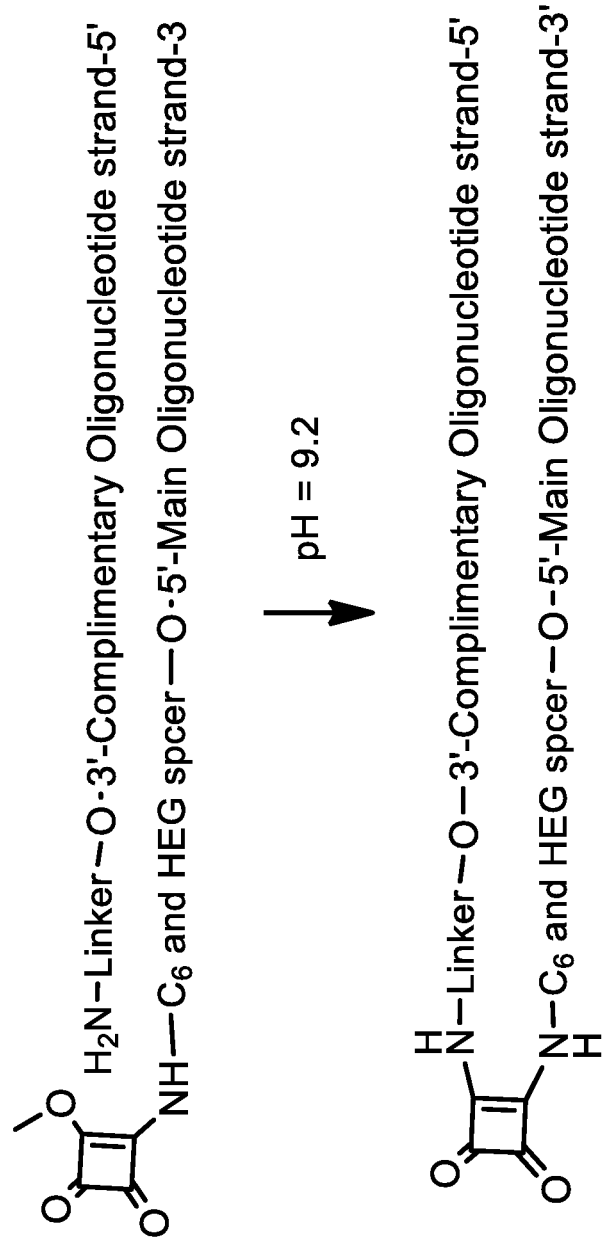
FIG. 5 shows conjugation of two complimentary RNA stands, one with a 5' amine, the other with a 3' amine using the described squarate coupling procedure

The complimentary sequence to the one mentioned in the above section (0074) was made using the same standard synthesis protocols used, in this case with a 3' amino linker attached, see FIG. 5. The modified RNA was deprotected, purified, ultrafiltered and lyophilized using the same procedures as used in the preparation of the 5' amino labeled RNA. 10 mg of the lyophilized 5'amino RNA was dissolved in 400 uL of water. 11 mg (approx. 1.2 fold excess) of the lyophilized 3' amino RNA compliment was dissolved in a separate 400 uL of water. The two solutions were combined and warmed to 50-60° C. for approximately 5 minutes, the solution was allowed to cool to room temperature over 30 minutes. To this solution was then added 300 uL of 150 mM sodium borate which brought the solution pH to approximately 9 (by pH paper). This mixture was allowed to stand at room temperature for 3 hours. LCMS analysis of a sample of this reaction showed that the dimer had been cleanly formed, with no hydrolyzed mono RNA squarate observed.

Conjugates of Two Oligonucleotides

In addition, the stability of mono conjugates of squarate with oligonucleotides (e.g., DNA or RNA) permits one to isolate the mono-conjugate intermediates and use them to couple with a second oligonucleotide, even if the second amino-labeled oligonucleotide is not complementary to the sequence of the oligonucleotide-squarate mono adduct. The coupling of two non-complimentary oligonucleotides (particularly when one oligonucleotide is DNA and the other is RNA) is very difficult to do non-enzymatically. Methods of the invention would provide access to these molecules.

Formation of Cyclic Oligonucleotides

As noted above, the stability of mono conjugates of squarate with oligonucleotides (e.g., DNA or RNA) permits one to isolate the mono-conjugate intermediates and use them to couple with a second oligonucleotide later. One may take advantage of this property and use these mono-conjugates to conjugate with second amino groups (which may be temporarily protected during the first stage of the conjugation) present at the other terminus of the oligonucleotides to form cyclic oligonucleotides.

Conjugation with Secondary Amines

Oligonucleotide Mono Squarate Conjugation with Peptides

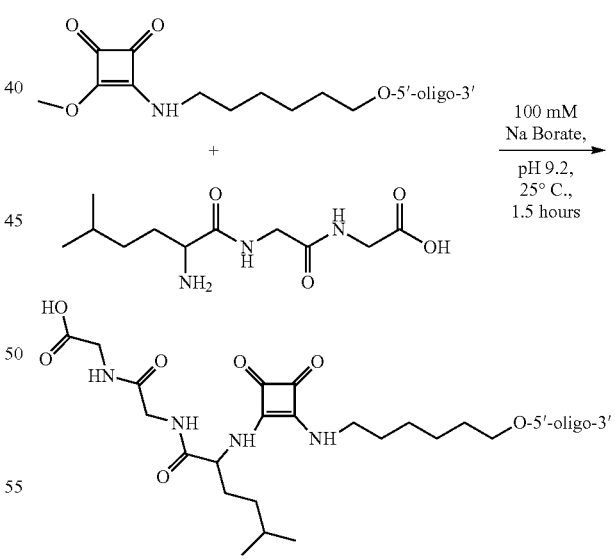

Figure 6:
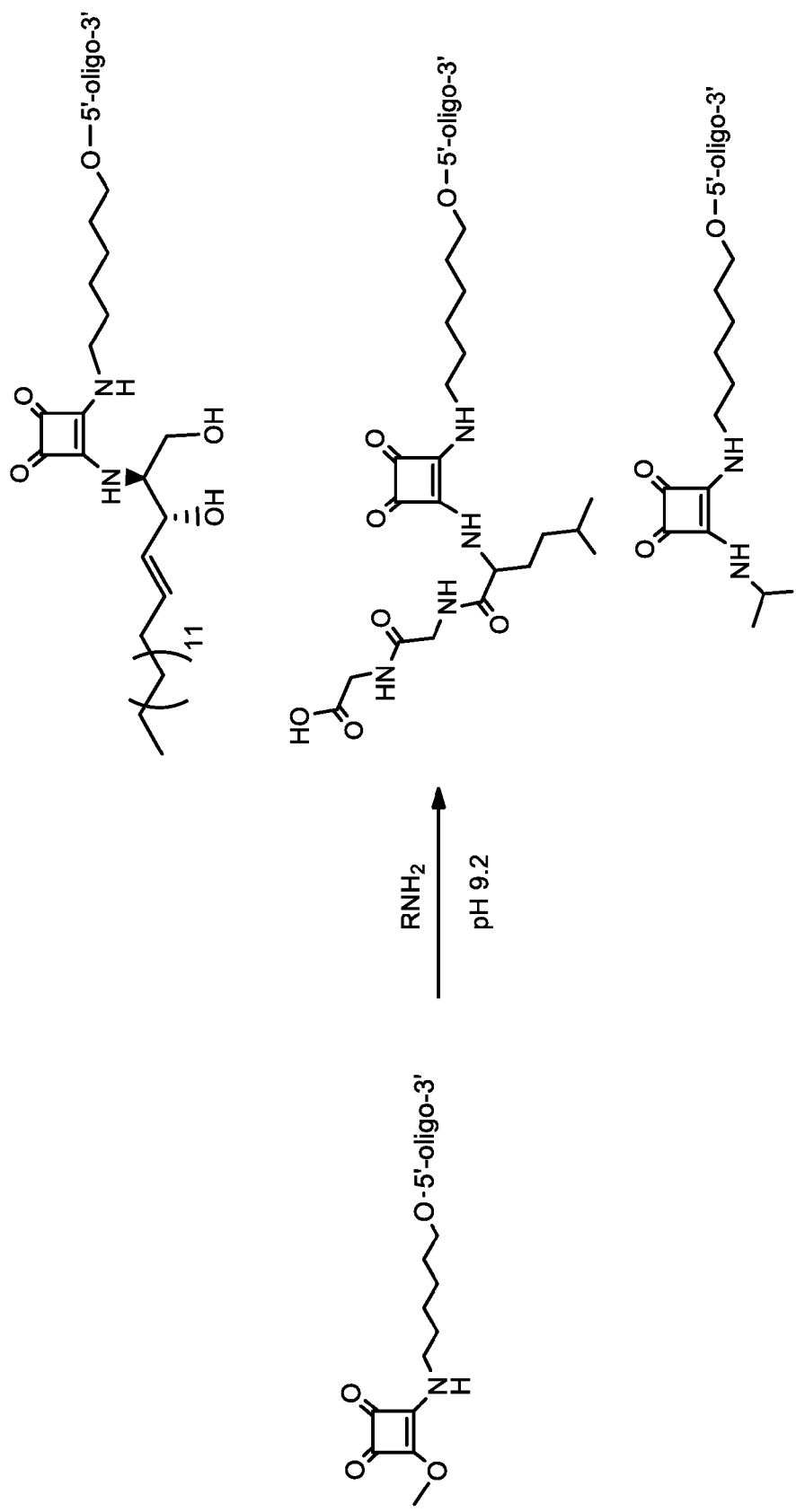
FIG. 6 shows conjugation of an oligonucleotide-squarate mono-adduct with various secondary amine target entities in accordance with embodiments of the invention.

To 100 μL of a 100 mM sodium borate buffered solution (pH=9.2) of the mono methoxy squarate labeled RNA 20 mer, approximately 1 μM, was added and excess of the tripeptide, Leu-Gly-Gly, dissolved 100 μL of 100 mM sodium borate buffered solution (pH=9.2). This mixture left at 25° C. for 1.5 hours. LCMS analysis of the reaction mixtures showed that the peptide conjugate was produced in approximately 85% yield, also see FIG. 6.

Oligonucleotide Mono Squarate Conjugation with Lipids

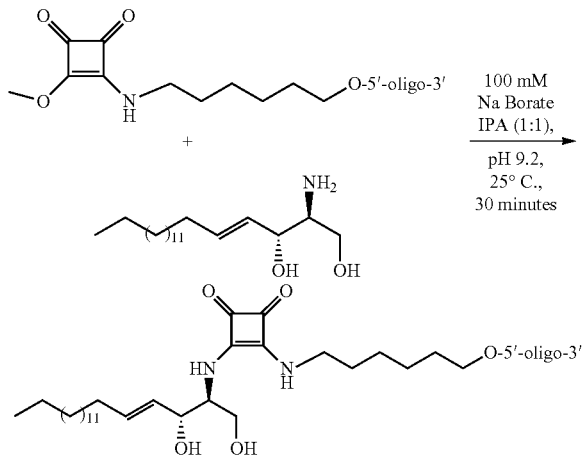

To 75 μL of 100 mM sodium borate buffered solution (pH=9.2) of the mono methoxy squarate labeled RNA 20 mer, at approximately 1 μM, was added a small excess of shpingosine dissolved 75 μL of isopropanol. This mixture left at 25° C. for 30 minutes. LCMS analysis of the reaction mixtures showed that the lipid conjugate was produced in approximately 60% yield, also see FIG. 6.

Oligonucleotide Mono Squarate Conjugation with Isopropyl Amine

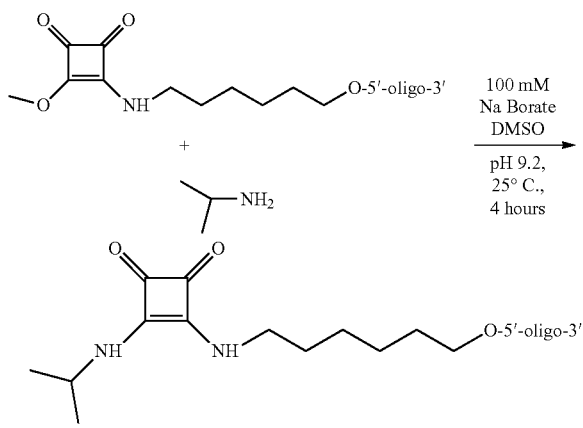

To 150 μL of a 100 mM sodium borate buffered solution (pH=9.2) of the mono methoxy squarate labeled RNA 20 mer, approximately 1 μM, was added and excess of isopropyl amine dissolved 20 μL of DMSO. After 4 hours at 25° C. LCMS analysis of the reaction mixtures showed that the isopropyl amine derivative was formed in over 95% yield, also shown in FIG. 6.

It is noted that the amino/thio labeled oligonucleotide can be added to an already derivatized mono squarate, inverting the order of addition. The mono squarate of a small molecule amine/thio, or peptide, protein, etc. can be made first and then treated with an amino/thio labeled oligonucleotide to form the squarate oligonucleotide conjugate.

In this specification and the appended claims, the singular forms "a," "an," and "the" include plural reference, unless the context clearly dictates otherwise.

Unless defined otherwise, all technical and scientific terms used herein have the same meaning as commonly understood by one of ordinary skill in the art. Although any methods and materials similar or equivalent to those described herein can also be used in the practice or testing of the present disclosure, the preferred methods and materials are now described. Methods recited herein may be carried out in any order that is logically possible, in addition to a particular order disclosed.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

INCORPORATION BY REFERENCE

References and citations to other documents, such as patents, patent applications, patent publications, journals, books, papers, web contents, have been made in this disclosure.

All such documents are hereby incorporated herein by reference in their entirety for all purposes. Any material, or portion thereof, that is said to be incorporated by reference herein, but which conflicts with existing definitions, statements, or other disclosure material explicitly set forth herein is only incorporated to the extent that no conflict arises between that incorporated material and the present disclosure material. In the event of a conflict, the conflict is to be resolved in favor of the present disclosure as the preferred disclosure.

EQUIVALENTS

The representative examples disclosed herein are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples which follow and the references to the scientific and patent literature cited herein. The following examples contain important additional information, exemplification and guidance that can be adapted to the practice of this invention in its various embodiments and equivalents thereof.

What is claimed is:

1. An oligonucleotide derivative having the structure of formula (A):

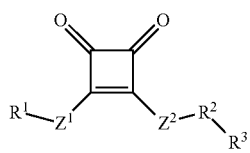

wherein $R^3$ is a first oligonucleotide; $R^1$ is selected from the group consisting of alkyl, cycloalkyl, aryl, heterocyclyl, and heteroaryl; $R^2$ is a selected from a ($C_1$-$C_{12}$) hydrocarbyl chain and a polyethylene glycol linker attached to a 5' hydroxy group, a 3' hydroxy group, or an exocyclic amino group on a nucleobase of the first oligonucleotide, wherein ($C_1$-$C_{12}$) hydrocarbyl chain is optionally substituted with a group selected from —O—R", —O—CO—R", —NR'—R", —NR'—CO—R", —CO—NR'—R", —CO—R", —CN, halogen, or a combination thereof, wherein R' and R" are independently H or ($C_1$-$C_6$) hydrocarbyl; $Z^1$ is S, or O, and $Z^2$ is $NR^4$ or S, wherein $R^4$ is selected from H, alkyl, aryl, heterocyclyl, or heteroaryl.

2. The oligonucleotide derivative of claim 1, wherein $R^2$ is attached to a 5' hydroxy group, or a 3' hydroxy group of the first oligonucleotide.

3. The oligonucleotide derivative of claim 1, wherein $Z^2$ is NH.

4. The oligonucleotide derivative of claim 1, wherein $R^1$ is a ($C_1$-$C_{12}$) alkyl and $Z^1$ is O.

5. The oligonucleotide derivative of claim 1, wherein $R^2$ is a ($C_1$-$C_{12}$) alkyl.

6. The oligonucleotide derivative of claim 1, wherein $R^2$ is a hexaethylene glycol linker.

7. A compound having the structure of formula (A):

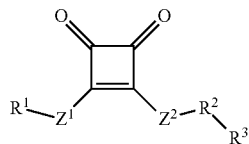

wherein $R^3$ is a first oligonucleotide; $R^1$ is selected from the group consisting of a polyethylene glycol, a peptide, a protein, a polysaccharide, a lipid and a second oligonucleotide; $R^2$ is a selected from an ($C_1$-$C_{12}$) hydrocarbyl chain and a polyethylene glycol linker attached to a 5' hydroxy group, a 3' hydroxy group, or an exocyclic amino group on a nucleobase of the first oligonucleotide, wherein the ($C_1$-$C_{12}$) hydrocarbyl chain is optionally substituted with —O—R", —O—CO—R", —NR'—R", —NR'—CO—R", —CO—NR'—R", —CO—R", —CN, halogen, or a combination thereof, wherein R' and R" are independently H or ($C_1$-$C_6$) hydrocarbyl; $Z^1$ is $NR^4$, S, or O, and $Z^2$ is $NR^4$ or S, wherein $R^4$ is selected from H, alkyl, aryl, heterocyclyl, or heteroaryl.

8. The compound of claim 7, wherein $R^1$ is a polyethylene glycol.

9. The compound of claim 7, wherein $R^1$ is a peptide or a protein.

10. The compound of claim 7, wherein $R^1$ is a second oligonucleotide.

11. The compound of claim 10, wherein the second oligonucleotide is complementary to the first oligonucleotide.

12. The compound of claim 7, wherein each of $Z^1$ and $Z^2$ is NH.

13. The compound of claim 7, wherein $Z^1$ is O and $Z^2$ is NH.

14. The compound of claim 7, wherein $R^1$ is a lipid.

15. The compound of claim 7, wherein $R^2$ is attached to a 5' hydroxy group, or a 3' hydroxy group of the first oligonucleotide.

16. The compound of claim 7, wherein $R^2$ is a ($C_1$-$C_{12}$) alkyl.

17. The compound of claim 7, wherein $R^2$ is a hexaethylene glycol linker.

* * * * *

UNITED STATES PATENT AND TRADEMARK OFFICE
CERTIFICATE OF CORRECTION

| | | |
|---|---|---|
| PATENT NO. | : 9,512,163 B2 | Page 1 of 2 |
| APPLICATION NO. | : 14/402220 | |
| DATED | : December 6, 2016 | |
| INVENTOR(S) | : Kenneth W. Hill et al. | |

It is certified that error appears in the above-identified patent and that said Letters Patent is hereby corrected as shown below:

On the Title Page

Item (57), in Column 2, in "Abstract", Line 3, delete "disclosed." and insert -- disclosed, --, therefor.

In the Specification

In Column 2, Line 64, after "procedure" insert -- . --.

In Column 5, Line 39, delete "8-quinoliyl," and insert -- 8-quinolinyl, --, therefor.

In Column 5, Line 40, delete "8-isoquinoliyl," and insert -- 8-isoquinolinyl, --, therefor.

In Column 5, Line 44, delete "8-carbzaolyl," and insert -- 8-carbazolyl, --, therefor.

In Column 5, Line 48, delete "10-phenathrolinyl," and insert -- 10-phenanthrolinyl, --, therefor.

In Column 5, Line 65, delete "heteroary" and insert -- heteroaryl --, therefor.

In Column 6, Line 36, delete "bicyciic" and insert -- bicyclic --, therefor.

In Column 6, Line 39, delete "heteocyclyl" and insert -- heterocyclyl --, therefor.

In Column 6, Line 41, delete "thiatanyl," and insert -- thietanyl, --, therefor.

In Column 6, Line 45, delete "tetrahydrothipyranyl," and insert -- tetrahydrothiopyranyl, --, therefor.

In Column 6, Line 47, delete "ptperidinyl," and insert -- piperidinyl, --, therefor.

In Column 6, Line 47, delete "morphoiinyl," and insert -- morpholinyl, --, therefor.

Signed and Sealed this
Twenty-eighth Day of February, 2017

Michelle K. Lee
*Director of the United States Patent and Trademark Office*

CERTIFICATE OF CORRECTION (continued)
U.S. Pat. No. 9,512,163 B2

In Column 6, Line 52, delete "morphoiinyl," and insert -- morpholinyl, --, therefor.

In Column 6, Line 52-53, delete "isoxazolinyi, A-ptperidony!, isoxazoiinyi," and insert -- isoxazolinyl, A-piperidonyl, isoxazolinyl, --, therefor.

In Column 6, Line 57, delete "thiamorphoiinyl suifone," and insert -- thiamorpholinyl sulfone, --, therefor.

In Column 6, Line 63, delete "tetrahydroisoquinoiinyl, decahydroisoquinoiinyl," and insert -- tetrahydroisoquinolinyl, decahydroisoquinolinyl, --, therefor.

In Column 6, Line 64, delete "indoiinyl, norboranyl," and insert -- indolinyl, norbornyl, --, therefor.

In Column 8, Line 36, delete "Gliisenkamp" and insert -- Glüsenkamp --, therefor.

In Column 10, Line 10, delete "$R_1$" and insert -- $R^1$ --, therefor.

In Column 11, Line 55, delete "mutimeric" and insert -- multimeric --, therefor.

In Column 15, Line 27, delete "shpingosine" and insert -- sphingosine --, therefor.

In the Claims

In Column 16, Line 64, in Claim 1, after "is" delete "a".

In Column 17, Line 1, in Claim 1, before "$(C_1-C_{12})$" insert -- the --.

In Column 17, Line 32, in Claim 7, after "is" delete "a".